United States Patent
Sircar et al.

(12)

(10) Patent No.: US 6,271,390 B1
(45) Date of Patent: *Aug. 7, 2001

(54) SUPPRESSION OF THE IGE-DEPENDENT ALLERGIC RESPONSE BY BENZIMIDAZOLE ANALOGS

(75) Inventors: Jagadish C. Sircar, San Diego; Mark L. Richards, La Jolla, both of CA (US); Michael G. Campbell, Durham, NC (US); Michael W. Major, Glendale, WI (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,870

(22) Filed: May 21, 1999

Related U.S. Application Data

(60) Provisional application No. 60/086,494, filed on May 22, 1998.

(51) Int. Cl.⁷ .................. B07D 235/18; A61K 31/4184; A61N 11/06
(52) U.S. Cl. .................. 548/309.7; 514/394; 548/310.1; 548/310.7
(58) Field of Search ............................. 548/309.7, 310.7, 548/310.1; 514/394

(56) References Cited

FOREIGN PATENT DOCUMENTS

| | | |
|---|---|---|
| 0 221 346 | 5/1987 | (EP) . |
| 0 232 199A | 8/1987 | (EP) . |
| 0 469 477 | 2/1992 | (EP) . |
| 0 497 564 | 8/1992 | (EP) . |
| 0 700 906A | 3/1996 | (EP) . |
| 0 719 765 | 7/1996 | (EP) . |
| 0 719 765A | 7/1996 | (EP) . |
| WO 90 09989 | 9/1990 | (WO) . |
| WO 93 25517 | 12/1993 | (WO) . |
| WO 98 17267 | 4/1998 | (WO) . |

OTHER PUBLICATIONS

Pozdnyakov et al. "Mass Spectrometric study of dissociative ionization of low–molecular models of aromatic polyamides" Khim. Vys. Energ. (1987), 21(1), 38–44 Coden: Khvkao; ISSN: 0023–1193, 1987.*

S. Karag'ozov, Synthesis of N–acyl derivatives of 6–amino–1–4–benzodioxane STN International, vol. 39, No. 1989 pp. 5–8, Abstract only.

Ashton et al., "Now low–density lipoprotein receptor upregulatros acting via a novel mechanism", Journal of Medicinal Chemistry, vol. 39, Jan. 1, 1996, pp. 3343–3356.

B. V. Cheney et al., "Structure–activity correlations for a series of antiallergy agents. 3. Development of a quantitative model", Journal Med. Chem, vol. 26, No. 5, 1983, pp. 726–737.

I Yildir, "Synthesis of 2–(substitutedphenyl) benzimidazole derivatives and their sedative activity: Structure–activity relationship", Journal Fax. Gazi Uni., vol. 7, No. 2, 1990, pp. 111–114.

\* cited by examiner

*Primary Examiner*—Floyd D. Higel
(74) *Attorney, Agent, or Firm*—Knobbe, Martens, Olson & Bear LLP

(57) ABSTRACT

The present invention is directed to small molecule inhibitors of the IgE response to allergens which are useful in the treatment of allergy and/or asthma or any diseases where IgE is pathogenic.

15 Claims, No Drawings

SUPPRESSION OF THE IGE-DEPENDENT ALLERGIC RESPONSE BY BENZIMIDAZOLE ANALOGS

This application claims the benefit of U.S. Provisional Application No. 60/086,494 filed on May 22, 1998.

BACKGROUND OF THE INVENTION

This invention relates to small molecule inhibitors of the IgE response to allergens that are useful in the treatment of allergy and/or asthma or any diseases where IgE is pathogenic.

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $1.1 billion (Kelly, *Pharmacotherapy* 12:13S-21S (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Department of Health and Human Services; 1991, publication no. 91-3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first, early phase asthmatic response is triggered by allergens, irritants, or exercise. Allergens cross-link immunoglobulin E (IgE) molecules bound to receptors on mast cells, causing them to release a number of pre-formed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment of asthma; however, their efficacies vary markedly. Short-acting $\beta_2$-adrenergic agonists, terbutaline and albuterol, long the mainstay of asthma treatment, act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction, have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents have been developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects.

Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73–81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc. and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p.26). Genentech recently disclosed positive results from a 536 patient phase-II/II trials of its recombinant humanized monoclonal antibody, rhuMAB-E25 (BioWorld® Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistimines and decongestants), compared to placebo. An NDA filing for this product is projected to be in the year 2000. The positive results from anti-IgE antibody trials suggest that therapeutic strategies aimed at IgE down-regulation may be effective.

SUMMARY OF THE INVENTION

The present invention discloses several compounds that are active in down-regulating the IgE response to allergens and other provocative stimuli. One compound is disclosed for use in the treatment of a condition associated with an excess IgE level. The compound has a formula:

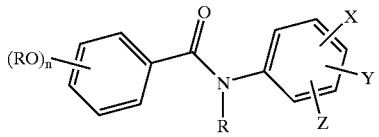

wherein n is 1 to 3 and wherein R is H, alkyl, aryl, aminoalkyl, alkylaminoalkyl, substituted aryl or hydroxyalkyl. X, Y and Z are selected independently from the group consisting of H, alkoxy, aryloxy, alkyl, aryl, heteroaryl, hydroxyalkyl, carboxy, amine, alkylamino, cycloalkylamine, morpholine, thiomorpholine, alkoxycarbonyl, hydroxy, cyano, sulfonamide, alkylsulfonamide, substituted aryl, substituted heteroaryl, trifluoromethyl, trifluoromethoxy, nitro, halogen, thioalkyl, sulfoxyalkyl and sulfonylalkyl.

Another compound for use in the treatment of a condition associated with an excess IgE level is disclosed in accordance with the present invention. The compound has a formula:

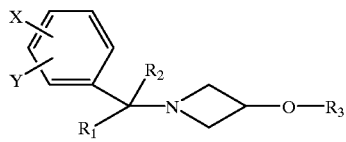

wherein X and Y are independently selected from the group consisting of H, alkyl, alkoxy, alkoxyalkyl, hydroxyalkyl, benzyl, aryl, heteroaryl, hydroxy, carboxy, halogen, trifluoromethyl, trifluoromethoxy, carboxyalkyl, nitro, cyano, alkylsulfonyl, sulfonamide, alkylsulfonamides, amino, alkylamino, morpholine, thiomorpholine, alkylthio, sulfoxyalkyl and sulfonylalkyl. $R_1$ and $R_2$ are independently selected from the group consisting of H, alkyl, aryl, heteroaryl, carboxy, carboxyalkyl and carboxyaryl. $R_3$ is selected from the group consisting of H, alkyl, aryl, CO-alkyl, CO-aryl and CO-heteroaryl.

Another compound for use in the treatment of a condition associated with an excess IgE level is disclosed in accordance with the present invention. The compound has a formula:

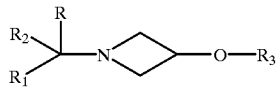

wherein $R_1$ and $R_2$ are independently selected from the group consisting of H, alkyl, aryl, heteroaryl, carboxy, carboxyalkyl and carboxyaryl. $R_3$ is selected from the group consisting of H, alkyl, aryl, CO-alkyl, CO-aryl, dialkylaminoalkyl, dialkylaminoalkylcarbonyl, substituted aryl, substituted heteroaryl and CO-heteroaryl, and R is selected from the group consisting of H, aryl, heteroaryl, substituted aryl and substituted heteroaryl.

Another compound for use in the treatment of a condition associated with an excess IgE level is disclosed in accordance with the present invention. The compound has a formula:

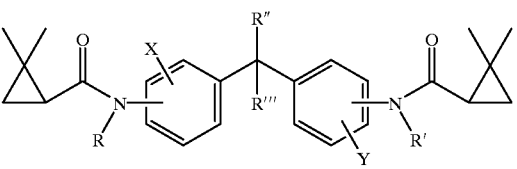

wherein X and Y are independently H, halogens, alkyl, alkoxy, alkoxyalkyl, aryl, substituted aryl, heteroaryl, substituted heteroaryl, trifluoromethyl, trifluoromethoxy, cyano, nitro, amino, acylamino or alkylamino. R, R', R" and R''' are independently H, alkyl, alkoxyalkyl or dialkylaminoalkyl, and R" and R''' may independently also be a halogen.

A preferred variation on the cyclopropyl-substituted compound above is illustrated by the formula:

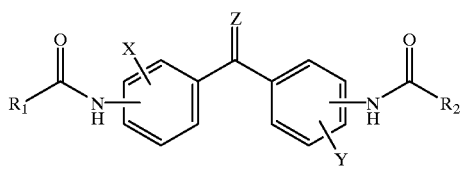

wherein Z is $H_2$ or O. X and Y are independently selected from the group consisting of H, halogens, alkyl, alkoxy, alkoxyalkyl, aryl, substituted aryl, heteroaryl, substituted heteroaryl, trifluoromethyl, trifluoromethoxy, cyano, nitro, amino, acylamino and alkylamino. $R_1$ and $R_2$ may be selected independently from the group consisting of H, alkyl, alkoxyalkyl, dialkylaminoalkyl, cycloalkyl, substituted cycloalkyl, aryl, substituted aryl, heteroaryl, and substituted heteroaryl.

A related compound for use in the treatment of a condition associated with an excess IgE level is disclosed in accordance with the present invention. The compound has a formula:

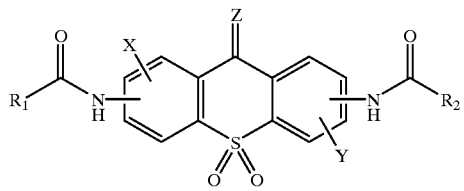

wherein Z is $H_2$ or O. X and Y are independently selected from the group consisting of H, halogens, alkyl, alkoxy, alkoxyalkyl, aryl, substituted aryl, heteroaryl, substituted heteroaryl, trifluoromethyl, trifluoromethoxy, cyano, nitro, amino, acylamino and alkylamino. $R_1$ and $R_2$ are selected independently from the group consisting of H, alkyl, alkoxyalkyl, dialkylaaminoalkyl, cycloalkyl, substituted cycloalkyl, aryl, substituted aryl, heteroaryl and substituted heteroaryl.

Another compound for use in the treatment of a condition associated with an excess IgE level is disclosed in accordance with the present invention. The compound has a formula:

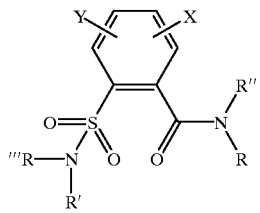

wherein X and Y are selected independently from the group consisting of H, halogens, alkyl, alkoxy, aryl, amino, alkylamino, cycloalkylamino, morpholine, thiomorpholine, hydroxy, cyano, nitro, carboxy, alkoxycarbonyl, tnfluoromethyl and tnifluoromethoxy. R, R', R" and R'" are selected independently from the group consisting of H, alkyl, aryl, cycloalkyl, substituted cycloalkyl, polycycloalkyl, heteroaryl, arylalkyl, dialkylaminoalkyl and hydroxyalkyl.

Another compound for use in the treatment of a condition associated with an excess IgE level is disclosed in accordance with the present invention. The compound has a formula:

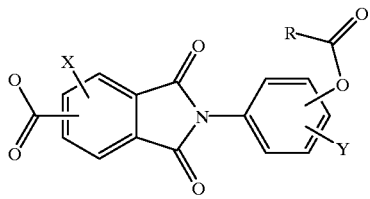

wherein R is selected from the group consisting of aliphatic, aromatic, heterocyclic, substituted aromatic and substituted heterocyclic. X and Y are independently selected from the group consisting of H, halogen, alkyl, alkoxy, aryl, substituted aryl, heteroaryl, substituted heteroaryl, hydroxy, nitro, trifluoromethyl, trifluoromethoxy and cyano.

Another compound for use in the treatment of a condition associated with an excess IgE level is disclosed in accordance with the present invention. The compound has a formula:

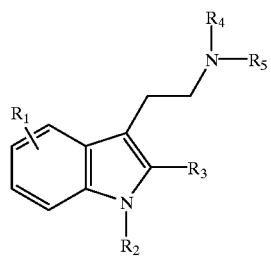

wherein $R_1$ is selected from the group consisting of H, halogen, alkoxy, alkyl, nitro, cyano, amino, $CF_3$, $OCF_3$ and hydroxy. $R_2$ is selected from the group consisting of H, alkyl and aminoalkyl, $R_3$ is H or alkyl, and $R_4$ and $R_5$ are independently selected from the group consisting of H, alkyl, aryl, heteroaryl, substituted aryl, substituted heteroaryl, cycloalkyl, aryl, aminocycloalkyl, hydroxyalkyl and substituted aryl.

Another compound for use in the treatment of a condition associated with an excess IgE level is disclosed in accordance with the present invention. The compound has a formula:

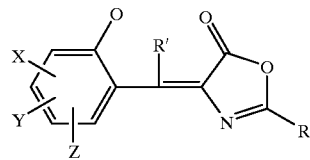

wherein R and R' are selected independently from the group consisting of H, methyl, alkyl, aryl and substituted aryl. X, Y and Z are independently selected from the group consisting of H, halogen, alkyl, alkoxy, benzo, fused heterocyclic, $CF_3$, $OCF_3$, CN, COOH and COOR".

Another compound for use in the treatment of a condition associated with an excess IgE level is disclosed in accordance with the present invention. The compound has a formula:

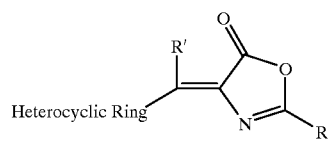

wherein the heterocyclic ring is selected from the group consisting of pyridines, quinolines, substituted pyridines and substituted quinolines. R and R' are independently selected from the group consisting of H, methyl, alkyl, aryl and substituted aryl.

Another compound for use in the treatment of a condition associated with an excess IgE level is disclosed in accordance with the present invention. The compound has a formula:

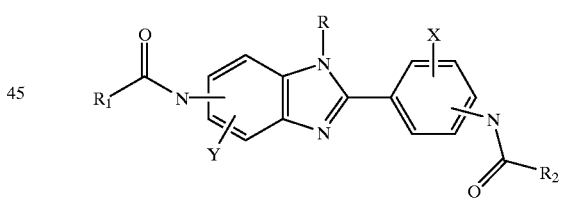

wherein X and Y are independently selected from the group consisting of H, halogen, alkyl, alkoxy, aryl, substituted aryl, hydroxy, amino, alkylamino, cycloalkyl, morpholine, thiomorpholine, nitro, cyano, $CF_3$ and $OCF_3$. R is selected from the group consisting of H, $CH_3$, $C_2H_5$, $C_3H_7$ and $C_4H_9$, and $R_1$ and $R_2$ are selected independently from the group consisting of H, methyl, ethyl, butyl, benzyl, substituted benzyl, dialkylaninoalkyl, alkyl, cycloalkyl, substituted cycloalkyl, polycycloalkyl, substituted fused cycloalkyl, aryl, substituted aryl, heteroaryl and substituted heteroaryl.

Another compound for use in the treatment of a condition associated with an excess IgE level is disclosed in accordance with the present invention. The compound has a formula:

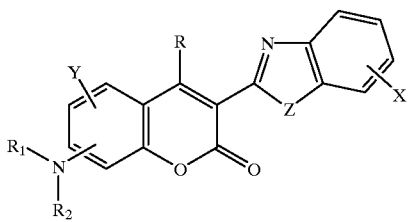

wherein X and Y are selected independently from the group consisting of H, alkyl, alkoxy, aryl, substituted aryl, heteroaryl, substituted heteroaryl, hydroxy, halogen, $NO_2$, $CF_3$, $OCF_3$, $NH_2$, $NHR_3$, $NR_3R_4$ and CN. Z is O, S, NH, and N—R'. R is selected from the group consisting of H, alkyl, halogen, alkoxy, $CF_3$ and $OCF_3$. R' is selected from the group consisting of H, alkyl, aminoalkyl, and dialkylaminoalkyl, and $R_1$ and $R_2$ are independently selected from the group consisting of H, alkyl, aminoalkyl, dialkylaminoalkyl, hydroxyalkyl, alkoxyalkyl, cycloalkyl, oxacycloalkyl and thiocycloalkyl.

Another compound for use in the treatment of a condition associated with an excess IgE level is disclosed in accordance with the present invention. The compound has a formula:

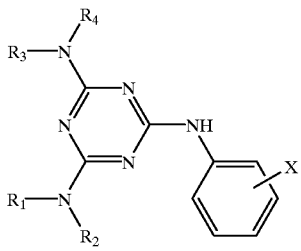

wherein $R_1$ and $R_2$ are selected independently from the group consisting of H, alkyl, aryl, heteroaryl, arylalkyl and heteroarylalkyl. X is selected from the group consisting of H, halogen, alkoxy, alkyl, $CF_3$, $NO_2$, CN and $OCF_3$. $R_3$ and $R_4$ are selected independently from the group consisting of H, alkyl, cycloalkyl, oxacycloalkyl and thiocycloalkyl.

Another compound for use in the treatment of a condition associated with an excess IgE level is disclosed in accordance with the present invention. The compound has a formula:

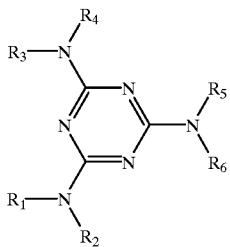

where $R_1$, $R_2$, $R_3$, $R_4$, $R_5$ and $R_6$ are selected independently from the group consisting of H, alkyl, cycloalkyl, oxacycloalkyl, thiocycloalkyl, aryl, arylalkyl, heteroaryl, heteroalkyl, substituted aryl and substituted heteroaryl.

Another compound for use in the treatment of a condition associated with an excess IgE level is disclosed in accordance with the present invention. The compound has a formula:

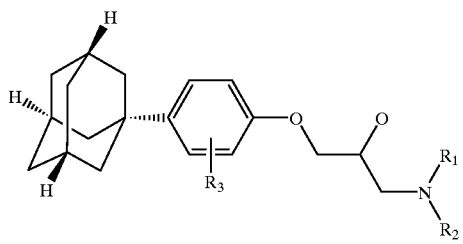

wherein $R_1$ and $R_2$ are independently selected from the group consisting of H, alkyl, aryl, alkylaryl, substituted alkyl, substituted arylalkyl, dialkyl and aminoalkyl. $R_3$ is selected from the group consisting of H, alkyl, aryl, halogen, $CF_3$, $OCF_3$, CN, $NO_2$, $NH_2$, NHR, carboxy, carboxyalkyl, alkoxy, heteroaryl, fused aryl and fused heteroaryl.

A method for treating a disease condition associated with excess IgE in a mammal is disclosed. The method comprises the step of administering to the mammal an IgE-suppressing amount of a pharmaceutical formulation comprising at least one IgE-suppressing compound from the above-disclosed small molecule families. In accordance with a variation of the method of treatment, the small molecule IgE-suppressing compound may be administered in conjunction with at least one additional agent, which is active in reducing a symptom associated with an allergic reaction. In one embodiment, the small molecule inhibitor may be mixed with at least one additional active ingredient to form a pharmaceutical composition. Alternatively, the small molecule inhibitor may be co-administered at the same time or according to different treatment regimens with the at least one additional active agent.

The at least one additional active ingredient may be a short-acting $\beta_2$-adrenergic agonist selected from the group consisting of terbutaline and albuterol; a long-acting $\beta_2$-adrenergic agonist selected from the group consisting of salneterol and formoterol; an antihistamine selected from the group consisting of loratadine, azelastine and ketotifen; a phosphodiesterase inhibitor, an anticholinergic agent, a corticosteroid, an inflammatory mediator release inhibitor or a leukotriene receptor antagonist.

A dose of about 0.01 mg to about 100 mg per kg body weight per day of the small molecule IgE inhibitory compound is preferably administered in divided doses for at least two consecutive days at regular periodic intervals.

A method for treating a disease condition associated with excess IgE in a mammal is also disclosed which comprises the step of administering to the mammal an IgE-suppressing amount of a pharmaceutical formulation comprising at least one compound selected from the following group of compounds:

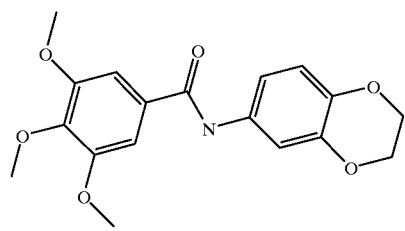

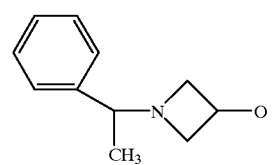
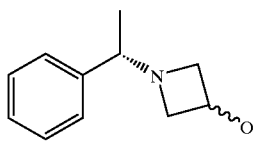
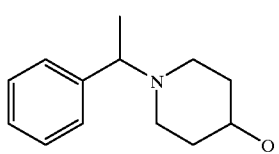
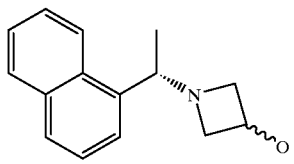
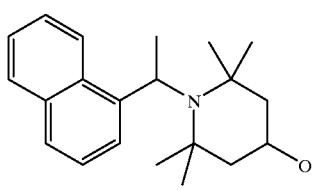
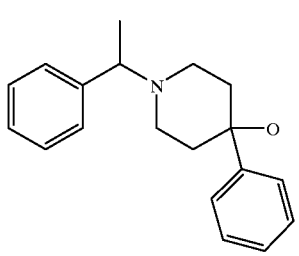
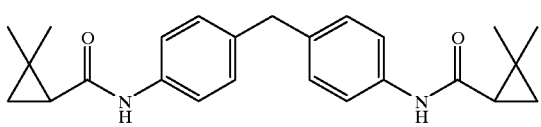
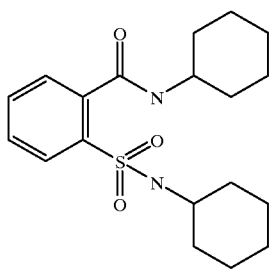
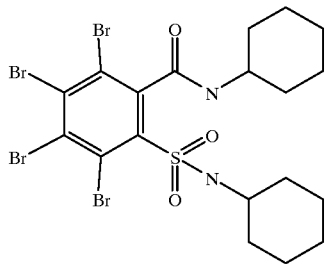
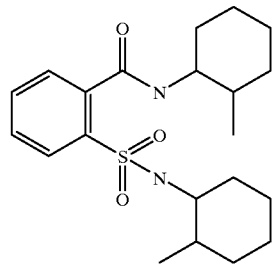
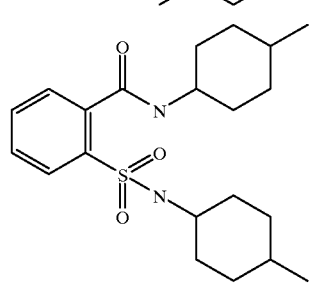
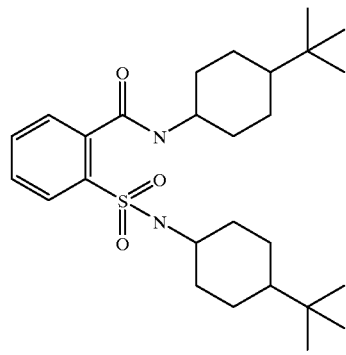
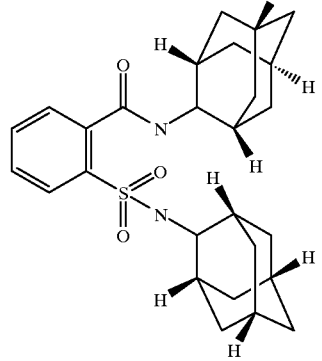

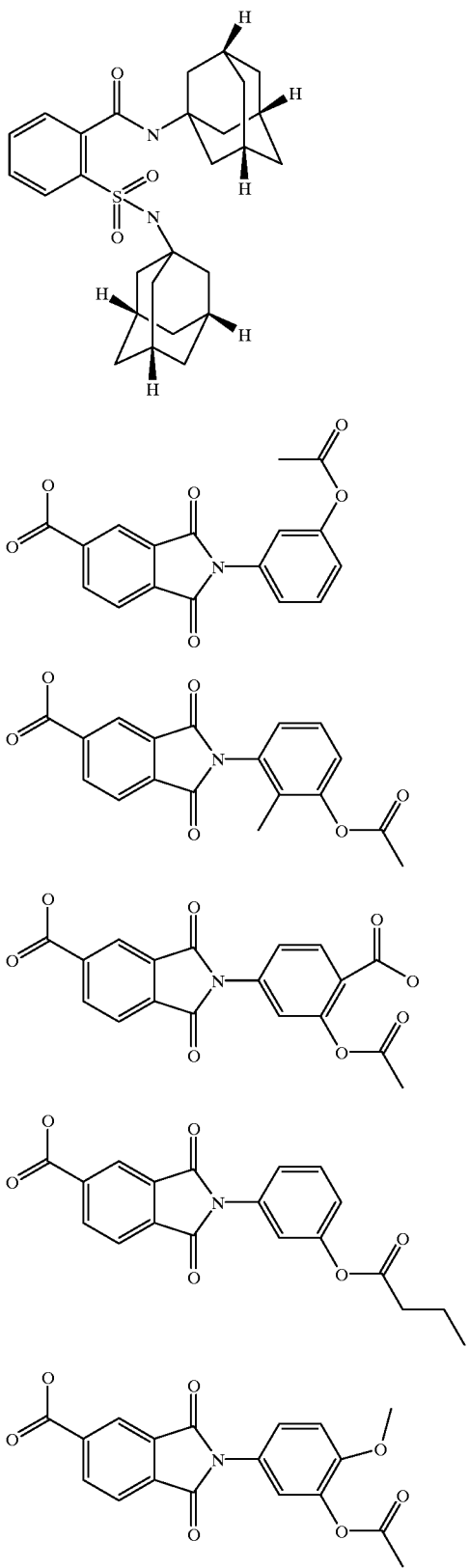
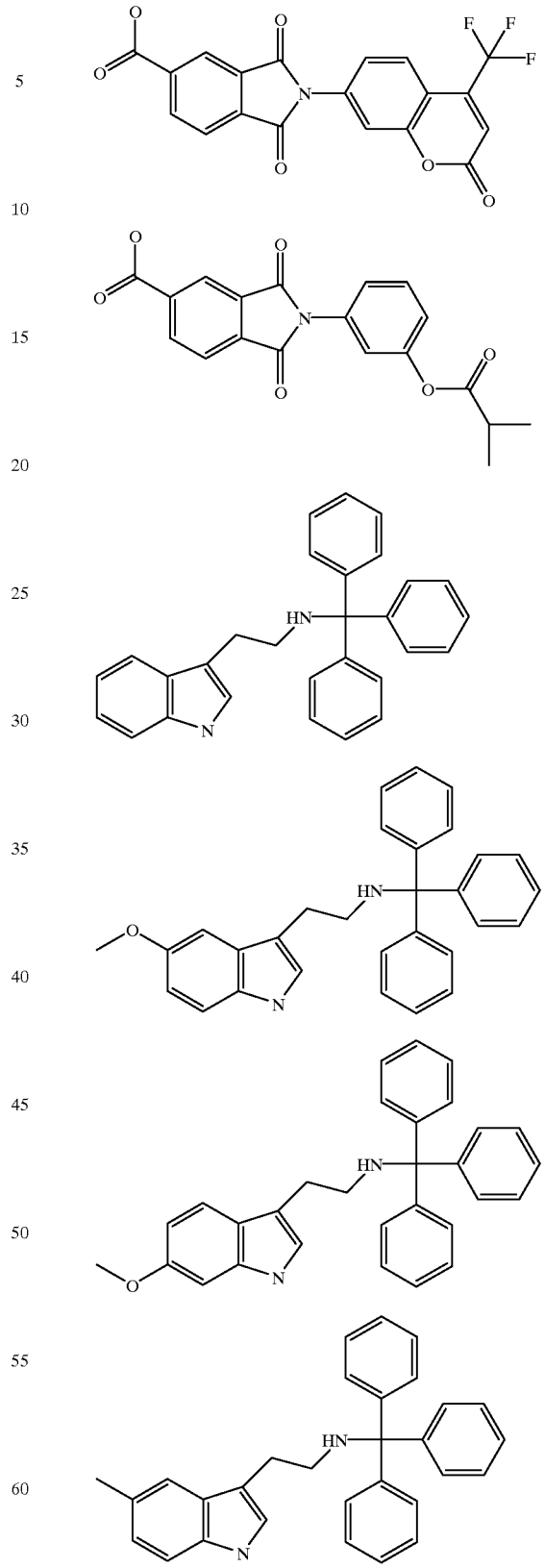

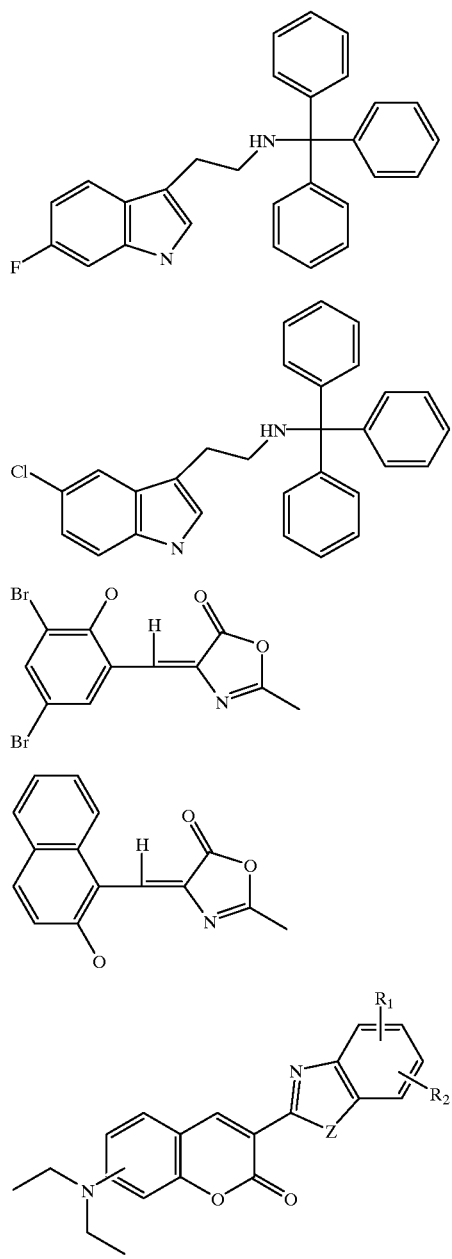

wherein Z is selected from the group consisting of NH, O, S and N—R';

wherein R' is selected from the group consisting of H, alkyl, aminoalkyl, and dialkylarninoalkyl;

wherein $R_1$ is selected from the group consisting of H, Cl and $SO_2CH_2CH_3$; and wherein R2 is selected from the group consisting of H, Cl, $CH_3$, $OCH_3$, COOH and $CF_3$, Other variations within the scope of the present invention may be more fully understood with reference to the following detailed description.

DETAILED DESCRIPTION OF THE PREFERRED EMBODIMENT

The present invention is directed to small molecule inhibitors of IgE (synthesis and/or release) which are useful in the treatment of allergy and/or asthma or any diseases where IgE is pathogenic. The particular compounds disclosed herein were identified by their ability to suppress IgE levels in both ex vivo and in vivo assays. Development and optimization of clinical treatment regimens can be monitored by those of skill in the art by reference to the ex vivo and in vivo assays described below.

Ex Vivo Assay

This system begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 135:471–489 (1991); incorporated herein by reference).

The actual protocol utilized for this project was adapted for a more high throughput analyses. BALB/cByj mice were immunized i.p. with 10 μg DNP-KLH adsorbed onto 4 mg alum and sacrificed after 15 days. Spleens were excised and homogenized in a tissue grinder, washed twice, and maintained in DMEM supplemented with 10% FBS, 100 μ/ml penicillin, 100 μg/ml streptomycin and 0.0005% 2-mercaptoethanol. Spleen cell cultures were established (2–3 million cells/ml, 0.2 ml/well in quadruplicate, 96-well plates) in the presence or absence of DNP-KLH (10 ng/ml). Test compounds (2 μg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype-selective ELISA assay described by Marcelletti and Katz (Supra). The assay was modified to facilitate high throughput. ELISA plates were prepared by coating with DNP-KLH overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IgG1 (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200–400 pg/ml and there was less than 0.001% cross-reactivity with any other Ig isotype in the ELISA for IgE.

In Vivo Assay

Compounds found to be active in the ex vivo assay (above) were fiurther tested for their activity in suppressing IgE responses in vivo. Mice receiving low-dose radiation prior to immunization with a carrier exhibited an enhanced IgE response to sensitization with antigen 7 days later. Administration of the test compounds immediately prior to and after antigen sensitization, measured the ability of that drug to suppress the IgE response. The levels of IgE, IgG1 and IgG2a in serum were compared.

Female BALB/cByj mice were irradiated with 250 rads 7 hours after initiation of the daily light cycle. Two hours later, the mice were immunized i.p. with 2 μg of KLH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5–6 mice. On the second day of drug administration, 2 μg of DNP-KLH was administered i.p. in 4 mg alum, immediately following the morning injection of drug. Mice were bled 7–21 days following DNP-KLH challenge. Antigen-specific IgE, IgG1 and IgG2a antibodies were measured by ELISA. Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Active Compounds of the Present Invention

The following series of compounds were found to be potent inhibitors of IgE in both ex-vivo and in vivo models.

One family of small molecule IgE inhibitors in accordance with the present invention include substituted benzanilides, defined by formula I:

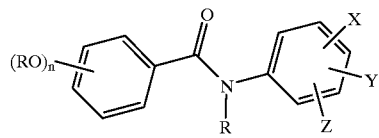

where n is 1 to 3, R is H, alkyl, aryl, aminoalkyl, alkylaminoalkyl, substituted aryl or hydroxyalkyl, and where X, Y and Z are selected independently from the group consisting of H, alkoxy, aryloxy, alkyl, aryl, heteroaryl, hydroxyalkyl, carboxy, amine, alkylamino, cycloalkylamine, morpholine, thiomorpholine, alkoxycarbonyl, hydroxy, cyano, sulfonamide, alkylsulfonamide, substituted aryl, substituted heteroaryl, trifluoromethyl, trifluoromethoxy, nitro, halogen, thioalkyl, sulfoxyalkyl, sulfonylalkyl or the like.

One compound encompassed within the definition of formula I, which was active in suppressing IgE, is represented by formula I.1:

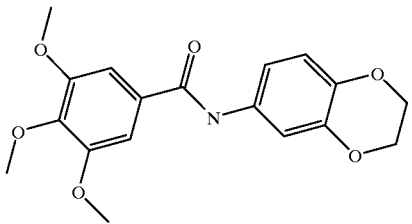

Compounds of formula I can be synthesized by the following reaction:

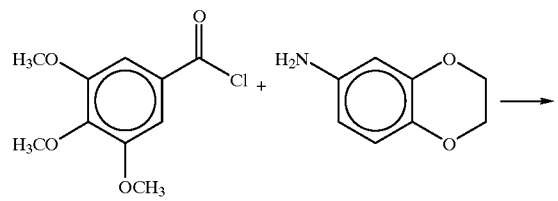

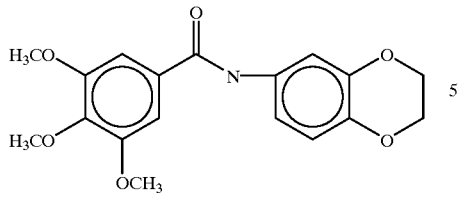

The reactants can be obtained from a commercial supplier, such as Aldrich Chemical Company, catalog numbers T6,980-9 and 19,323-2. Modifications as suggested by formula I can be prepared by conventional reactions, well known in the field.

Another family of small molecule IgE inhibitors is defined by generic formula II(1) below.

II(1)

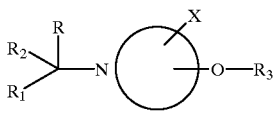

wherein X is a cycloalkyl or substituted cycloalkyl having from 4–6 carbons, where $R_1$ and $R_2$ are independently H, alkyl, aryl, heteroaryl, carboxy, carboxyalkyl and carboxyaryl, where $R_3$ is H, alkyl, aryl, CO-alkyl, CO-aryl, dialkylaminoalkyl, dialkylaminoalkylcarbonyl, substituted aryl, substituted heteroaryl and CO-heteroaryl, and where R is H, aryl, heteroaryl, substituted aryl, substituted heteroaryl or the like.

More preferably, the genus is represented by formula II(2).

II(2)

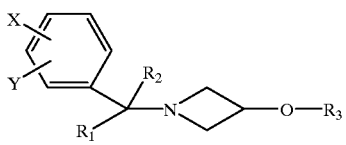

where X and Y are independently H, alkyl, alkoxy, alkoxyalkyl, hydroxyalkyl, aryl, benzyl, heteroaryl, hydroxy, carboxy, halogen, trifluoromethyl, trifluoromethoxy, carboxyalkyl, nitro, cyano, sulfonamide, alkylsulfonamides, amino, alkylamino, morpholine, thiomorpholine, alkylthio, sulfoxyalkyl and sulfonylalkyl, where $R_1$ and $R_2$ are independently H, alkyl, aryl, heteroaryl, carboxy, carboxyalkyl and carboxyaryl, and where $R_3$ is H, alkyl, aryl, CO-alkyl, CO-aryl or CO-heteroaryl.

The following compounds within the genus were synthesized and found to be active in suppressing IgE:

II.1

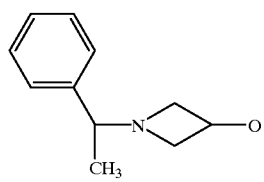

II.2

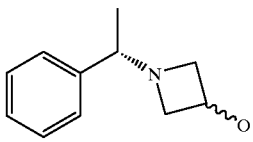

II.3

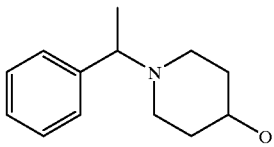

II.4

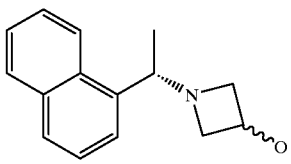

II.5

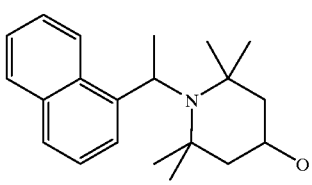

II.6

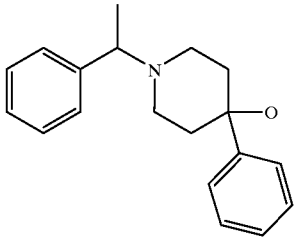

Compounds of formula II may be synthesized by any conventional reactions known in the art. Examples of syntheses include the following reactions:

A solution of DL-α-methyl-benzylamine (2.0 g, 0.017 mol) in MeOH (7.0 ml) and epichlorohydrine (1.53 g, 0.017 mol) in MeOH (7.0 ml) was stirred at room temperature for some time and then heated at about 45–50° C. for 3 days. The reaction mixture was basified with 10% NaOH solution and then extracted with ether (2×25 ml), ether layer washed with brine, concentrated and distilled. The yield was 1.507 g, b.p. 116–120° C.

The stereochemistry variation was achieved by stirring a solution of R-(+)-1-phenylethylamine (2.0 g, 0.017 mol) in 7.0 ml of MeOH with epichlorohydrine (1.53 g, 0.017 mol) in MeOH (7.0 ml). The reaction was carried out as detailed above.

The reactants can be obtained from a commercial supplier, such as for example, Aldrich Chemical Company, catalog number 16,854-8. Modifications as suggested by formulas II(1–2) can be prepared by conventional reactions, well known in the field.

Substituted benzene rings with acylamide groups are also contemplated in accordance with the present invention, as described by generic formula III:

III

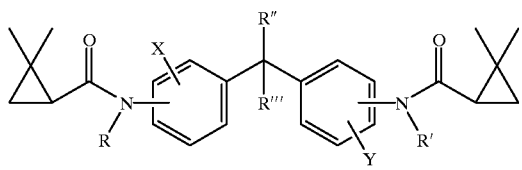

wherein X and Y are independently H, halogens, alkyl, alkoxy, alkoxyalkyl, aryl, substituted aryl, heteroaryl, substituted heteroaryl, trifluoromethyl, trifluoromethoxy, cyano, nitro, amino, acylamino or alkylamino, wherein R, R', R" and R'" are independently H, alkyl, alkoxyalkyl or dialkylaminoalkyl, and where R" and R'" may independently also be a halogen.

A preferred variation on compound III is illustrated by the formula:

III(1)

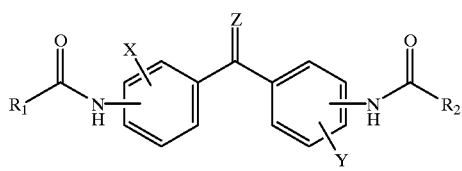

wherein Z is $H_2$ or O; wherein X and Y are independently selected from the group consisting of H, halogens, alkyl, alkoxy, alkoxyalkyl, aryl, substituted aryl, heteroaryl, substituted heteroaryl, trifluoromethyl, trifluoromethoxy, cyano, nitro, amino, acylamino and alkylamino; and wherein $R_1$ and $R_2$ may be selected independently from the group consisting of H, alkyl, alkoxyalkyl, dialkylaminoalkyl, cycloalkyl, substituted cycloalkyl, aryl, substituted aryl, heteroaryl, and substituted heteroaryl.

The following species of formula III(1) were synthesized and found to be active in suppressing IgE (see Table 1).

TABLE 1

| | $R_1 = R_2$ | Z | X = Y |
|---|---|---|---|
| III.1 | 2,2-dimethyl-cyclopropyl | O | H |
| III.2 | cyclopropyl | $H_2$ | H |
| III.3 | cyclohexyl | O | H |
| III.4 | 2,2,3,3-tetramethyl-cyclopropyl | $H_2$ | H |
| III.5 | 4-methyl-benzenesulfonyl | $H_2$ | H |
| III.6 | cyclobutyl | $H_2$ | H |
| III.7 | 2-phenyl-cyclopropyl | $H_2$ | H |
| III.8 | 1-phenyl-cyclopropyl | $H_2$ | H |
| III.9 | 2-methyl-cyclopropyl | $H_2$ | H |
| III.10 | 1-methyl-cyclopropyl | $H_2$ | H |
| III.11 | cyclopentyl | $H_2$ | H |
| III.12 | 2,2-dimethyl-cyclopropyl | $H_2$ | Cl |

The following symmetrical cyclopropyl compound within the genus was found to be particularly active in suppressing IgE:

III.1

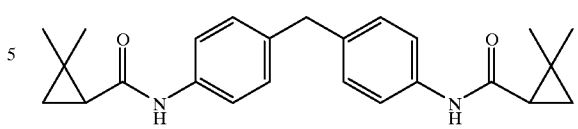

The cyclopropyl substituted compound above was prepared in sequential reactions. First, 2,2-dimethyl-1,3-propane-ditosylate was synthesized by adding p-toluenesulfonyl chloride (1000 g, 5.25 mol) at 0° C. to a solution of neopentyl glycol (218 g, 2.1 mol) in 500 ml pyridine with stirring. The mixture was stirred for 1.5 hr and then poured into 1500 ml water in a slow stream while stirring vigorously. It was stirred for an additional 1.5 hr and then filtered. The crude solid was recrystallized from acetone (2.0 L), filtered, washed with water (2×0.5 L), hexane (1×0.5 L) and dried. Snow white solid (814 g) m.p. 120–121° C.

2,2-Dimethyl-cyclopropyl nitrile was synthesized by stirring the 2,2-dimethyl-1,3-propane-ditosylate prepared above (412 g, 1.0 mol) with KCN (195.4 g, 3.0 mol) in 2.0 L of ethylene glycol with heating (E. R. Nelson et al., JACS, 1957, p. 3467). At around 80° C., a clear solution was formed. The desired product began to distill out at about 175° C. The distillation was continued until the temperature reached 200° C. The distillate (300 ml) formed two layers. The upper layer was separated and the lower layer was extracted with hexane (3×200 ml). The combined extracts were dried over Na2CO3, concentrated and re-distilled at normal pressure. The yield was 41.7 g (43.8%), b.p. 151–152° C.

2,2-Dimethyl-cyclopropyl carboxylic acid was prepared by mixing 2,2-dimethyl-cyclopropyl nitrile (41.7 g, 0.43 mol) with sodium hydroxide (44 g, 1.05 mol) in water (100 ml) and methanol (50 ml). The mixture was heated to reflux for 48 hr until a clear solution formed. Methanol was distilled off and the aqueous portion was extracted with ether (50 ml) and the aqueous layer was diluted with water (500 ml) and carefully acidified with conc. HCl. The acidified mixture was extracted with ether (5×300 ml), $CH_2Cl_2$ (5×300 ml). The extract was evaporated to yield a liquid which was distilled to give 44.9 g (91.6%) of oil, b.p. 55–57° C. at 0.3 mm.

2,2-Dimethyl-cyclopropyl carboxylic acid chloride was prepared by mixing 2,2-dimethyl-cyclopropyl carboxylic acid (20.0 g, 0.18 mol) in $CH_2Cl_2$ (100 ml) with 45.7 g (0.36 mol, 31.4 ml) of oxalyl chloride. The mixture was stirred for 1.0 hr and then a small amount of DMF was added to ensure the completion of the reaction. The mixture was then distilled to give 17.8 g (75%) of the desired product, b.p. 84–87° C.

Compound III.1, Bis-[4-(2',2'-dimethyl-cyclopropyl carboxy-amido phenol)]-methane, was prepared by combining a solution of 4,4'-methylenedianiline (0.67 g, 3.4 mol) and diisopropyl-ethyl-amine (1.94 g, 2.61 ml, 0.019 mol) in THF (10 ml). The mixture was treated slowly with a solution of 2,2-dimethyl-cyclopropyl carboxylic acid chloride (1.0 g, 7.5 mmol) in THF (10 ml). The reaction mixture was stirred for 1.0 hr and then decomposed with water (250 ml). The precipitated solid was filtered and washed with 10% HCl (10 ml), 10% sodium hydroxide (10 ml), water and ether. The yield was 1.2 g, m.p. 207–210° C.

Related compounds within the genus can be synthesized following the above reactions. A general synthetic scheme is outlined below:

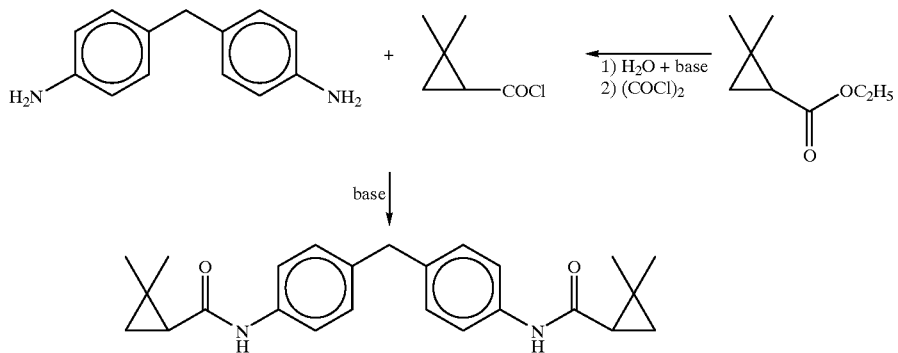

The reactants can be obtained from a commercial supplier, such as Aldrich Chemical Company, catalog number 13,245-4, and dialkylcyclopropane carboxylate is available from Sumitomo, Japan. Modifications as suggested by formulas III(1–4) can be prepared by conventional reactions, well known in the field.

A closely related genus of compounds was also found to active in down-regulating IgE levels. This class of compounds is represented by formula IV:

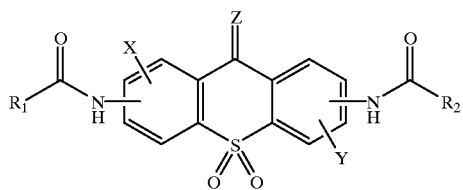

IV where Z is $H_2$ or O, and X and Y are independently selected from the group consisting of H, halogens, alkyl, alkoxy, alkoxyalkyl, aryl, substituted aryl, heteroaryl, substituted heteroaryl, trifluoromethyl, trifluoromethoxy, cyano, nitro, amino, acylamino and alkylamino. $R_1$ and $R_2$ may be selected independently from the group consisting of H, alkyl, alkoxyalkyl, dialkylaminoalkyl, cycloalkyl, substituted cycloalkyl, aryl, substituted aryl, heteroaryl, substituted heteroaryl, and the like.

A species wherein Z=$H_2$, X=H, Y=H and $R_1$=$R_2$= dimethyl-cyclopropyl was prepared from 3,6-thioxanthenediamine-10,10-dioxide (0.89 g) and 1.0 g of 2,2-dimethyl-cyclopropyl carboxyl chlorine (see above) in the presence of di-isopropyl-ethylamine (2.6 ml) in THF. The yield was 1.4 g, m.p. 273–275° C.

Another class of compounds which down-regulates IgE responses in accordance with the present invention is illustrated by the formula V:

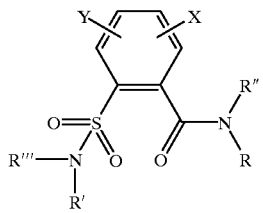

V wherein X and Y are independently H, halogens, alkyl, alkoxy, aryl, amino, alkylamino, cycloalkylamino, morpholine, thiomorpholine, hydroxy, cyano, nitro, carboxy, alkoxycarbonyl, trifluoromethyl or trifluoromethoxy, and R, R', R" and R'" are independently alkyl, aryl, cycloalkyl, cycloalkyl, substituted cycloalkyl, polycycloalkyl, heteroaryl, arylalkyl, dialkylaminoalkyl, hydroxyalkyl and related groups.

The following compounds encompassed within the family defined by formula V were prepared and found to be active in suppressing IgE:

V.1

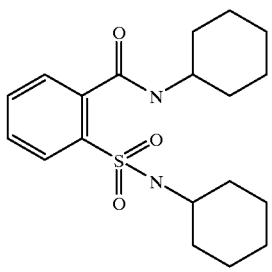

V.2

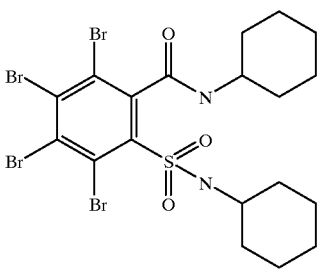

V.3

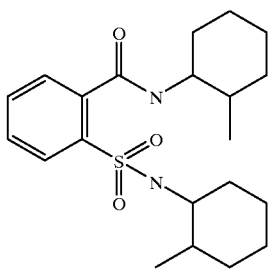

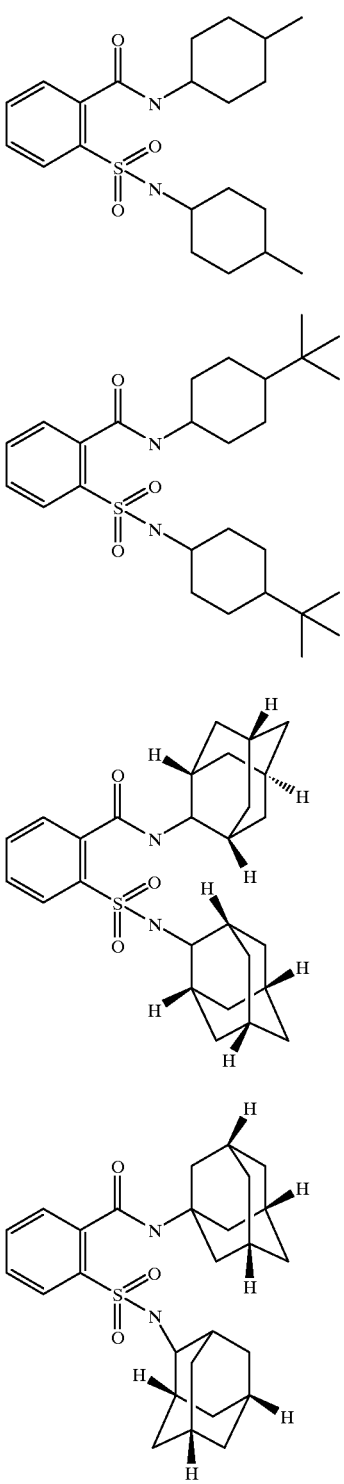

V.4

V.5

V.6

V.7

Compounds of formula V can be synthesized by any conventional reactions known in the art. The above species V.1–7 were synthesized by the following reaction, where the benzene ring can be substituted, as indicated by the X (e.g., bromide, as in V.2) and the amide is varied to yield the desired compounds:

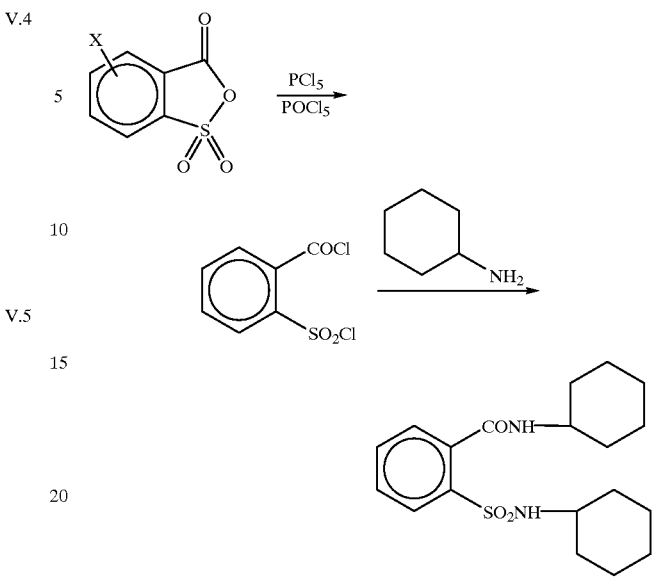

The reactants were obtained from commercial suppliers, such as Aldrich Chemical Company, catalog number 19,169-8. Modifications can be prepared by conventional reactions, well known in the field.

Another useful class of compounds is represented by the formula VI:

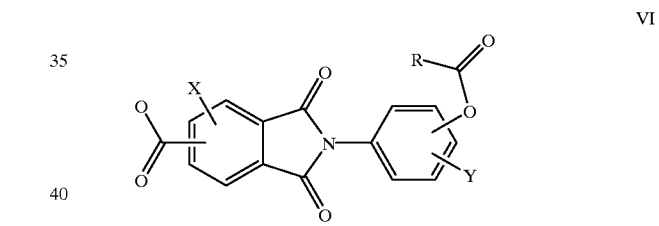

VI where R is aliphatic, aromatic, heterocyclic, substituted aromatic, substituted heterocyclic or the like, and where X and Y are independently, H, halogen, alkyl, alkoxy, aryl, substituted aryl, heteroaryl, substituted heteroaryl, hydroxy, nitro, trifluoromethyl, trifluoromethoxy, cyano or the like. Replacement of the carboxylic acid with other bioisosteric groups such as tetrazole and tetrazoleamide is also contemplated in accordance with the present invention.

The following compounds encompassed within the family defined by formula VI were prepared and found to be active in suppressing IgE:

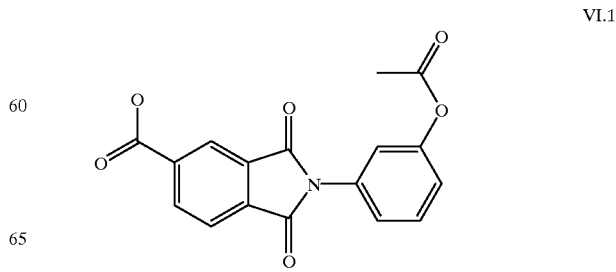

VI.1

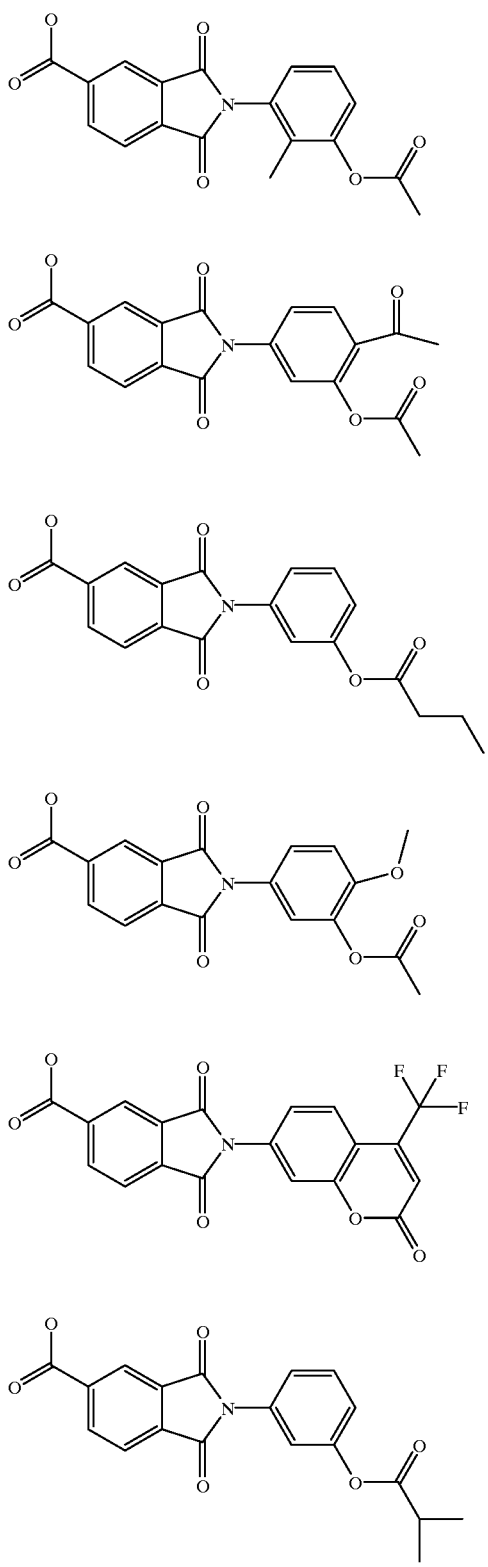

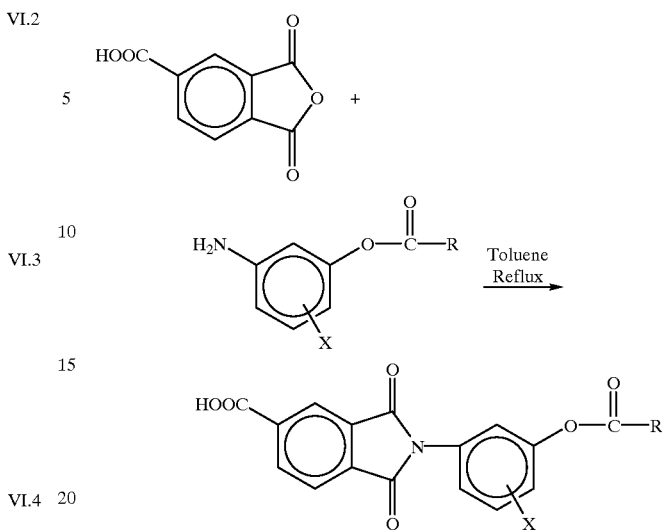

Where the reactants can be obtained from a commercial supplier, such as Aldrich Chemical Company, catalog numbers B460-0 and 10,080-3. Modifications can be prepared by conventional reactions, well known in the field.

Other small molecules active in suppressing IgE include those represented by formula VII.

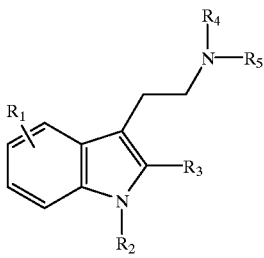

VII where $R_1$ is H, halogen, alkoxy, alkyl, nitro, cyano, amino, $CF_3$, $OCF_3$ or hydroxy, where $R_2$ is H, alkyl or aminoalkyl, where $R_3$ is H or alkyl, and where $R_4$ and $R_5$ are independently H, alkyl, aryl, heteroaryl, substituted aryl, substituted heteroaryl, cycloalkyl, aminocycloalkyl, aryl, hydroxyalkyl, substituted aryl or the like.

The following compounds encompassed within the family defined by formula VII were prepared and found to be active in suppressing IgE:

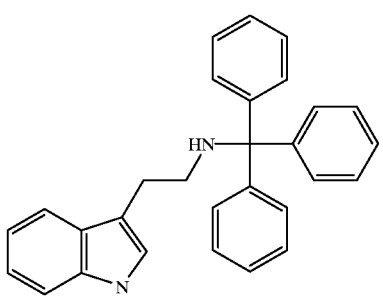

VII.1

Compounds of formula VI may be synthesized by any conventional reactions known in the art. One example of a synthesis reaction is shown below:

-continued

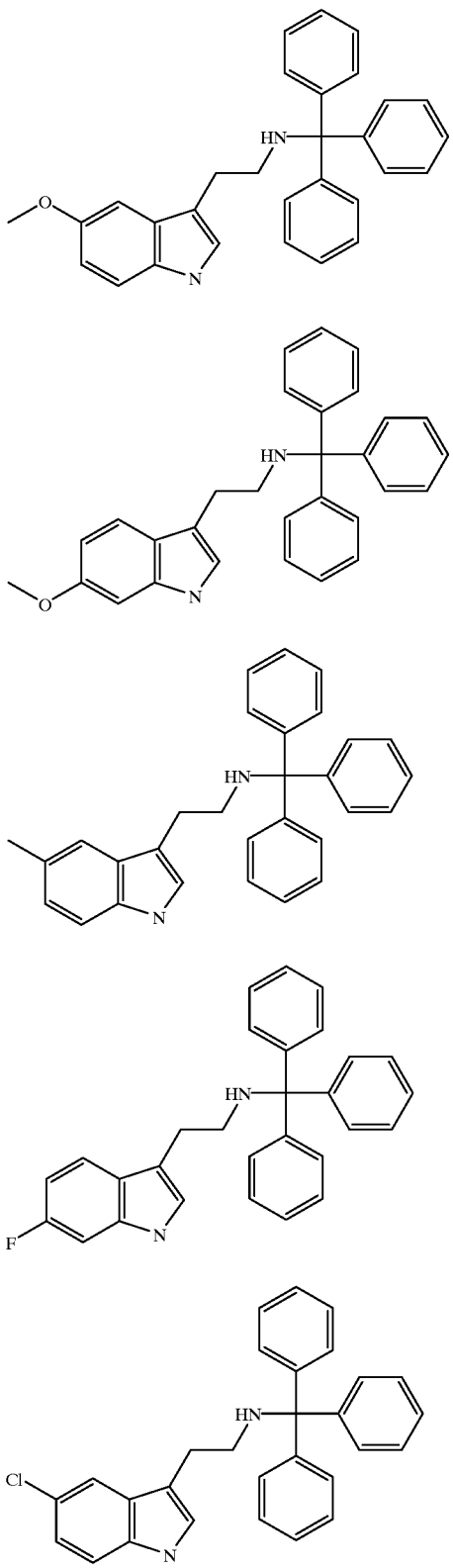

illustrated below, where X represents the different substitutions on the benzene ring:

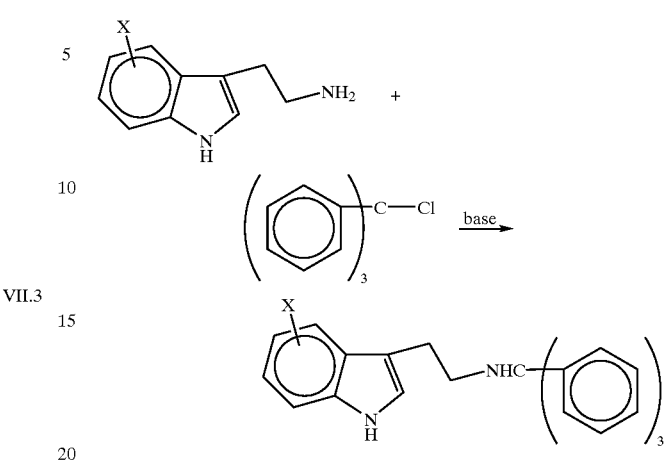

The reactants can be obtained from a commercial supplier, such as Aldrich Chemical Company, catalog numbers 19,374-2 and T8,380-1. Modifications can be prepared by conventional reactions, well known in the field.

Other substituted benzene ring molecules contemplated in accordance with the invention are illustrated by formula VIII(1):

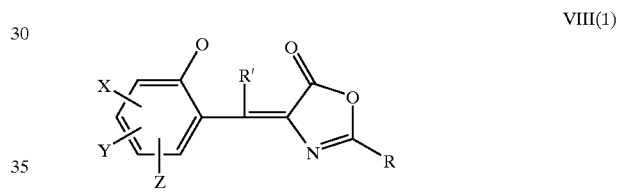

VIII(1)

where R and R' are selected independently from the group consisting of H, methyl, alkyl, aryl, substituted aryl, heteroaryl and substituted heteroaryl, and where X, Y and Z are independently H, halogen, alkyl, alkoxy, benzo, fused heterocyclic, $CF_3$, $OCF_3$, CN, nitro, COOH or COOR".

Compounds encompassed by formula VIII(1) were prepared and found to be active in suppressing IgE; they are represented by formulas VIII.1 and VIII.2:

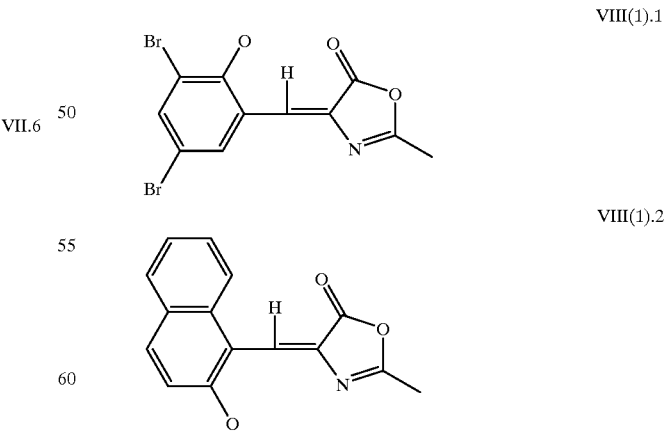

Compounds of formula VII may be synthesized by any conventional reactions known in the art. The compounds above (VII.1–6) were prepared according to the reaction Another useful class of compounds in accordance with the present invention represents a modification of formula VIII (1), by replacement of the benzene ring with a heterocyclic ring. These compounds are represented by formula VIII(2):

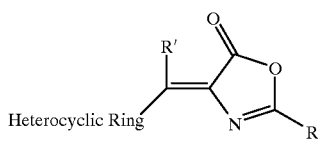

where the heterocyclic ring is pyridines, quinolines, substituted pyridines, substituted quinolines or other heterocyclic compounds, and where R and R' are independently H, methyl, alkyl, aryl or substituted aryl.

Compounds of formula VIII may be synthesized by any conventional reactions known in the art. An example of a synthesis reaction is shown below:

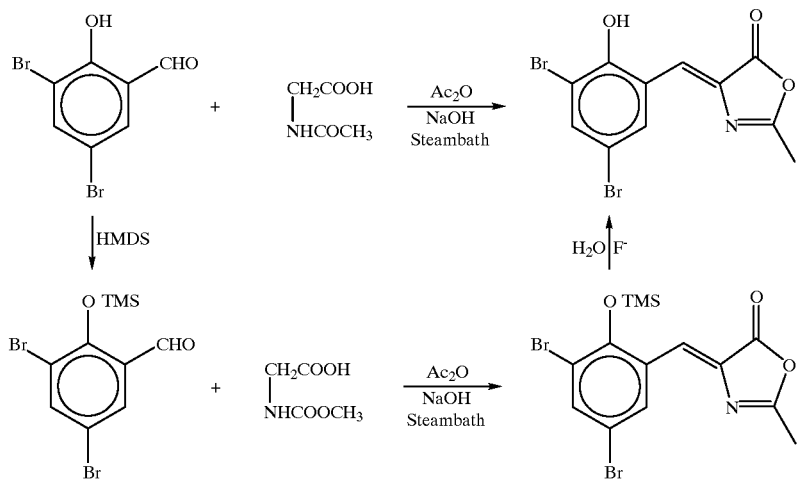

Where the reactant can be obtained from a commercial supplier, such as Aldrich Chemical Company, catalog number 12,213-0. Modifications can be prepared by conventional reactions, well known in the field.

Another compound effective in down-regulating IgE is formula IX:

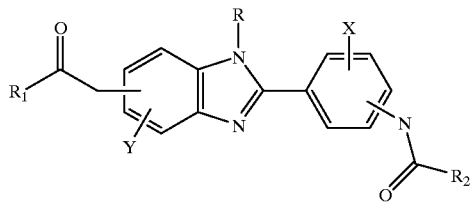

where X and Y may be different or the same and are independently selected from the group consisting of H, halogen, alkyl, alkoxy, aryl, substituted aryl, hydroxy, amino, alkylamino, cycloalkyl, morpholine, thiomorpholine, nitro, cyano, $CF_3$ or $OCF_3$, where R is H, $CH_3$, $C_2H_5$, $C_3H_7$ or $C_4H_9$, and where $R_1$ and $R_2$ are independently H, alkyl, cycloalkyl, substituted cycloalkyl, polycycloalkyl, substituted polycycloalkyl, aryl, substituted aryl, heteroaryl or substituted heteroaryl.

One compound encompassed by formula IX was prepared and found to be active in suppressing IgE; it is represented by formula IX.1:

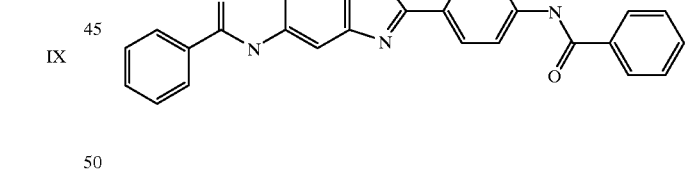

Compounds of formula IX may be synthesized by any conventional reactions known in the art. An example of a synthesis reaction is shown below:

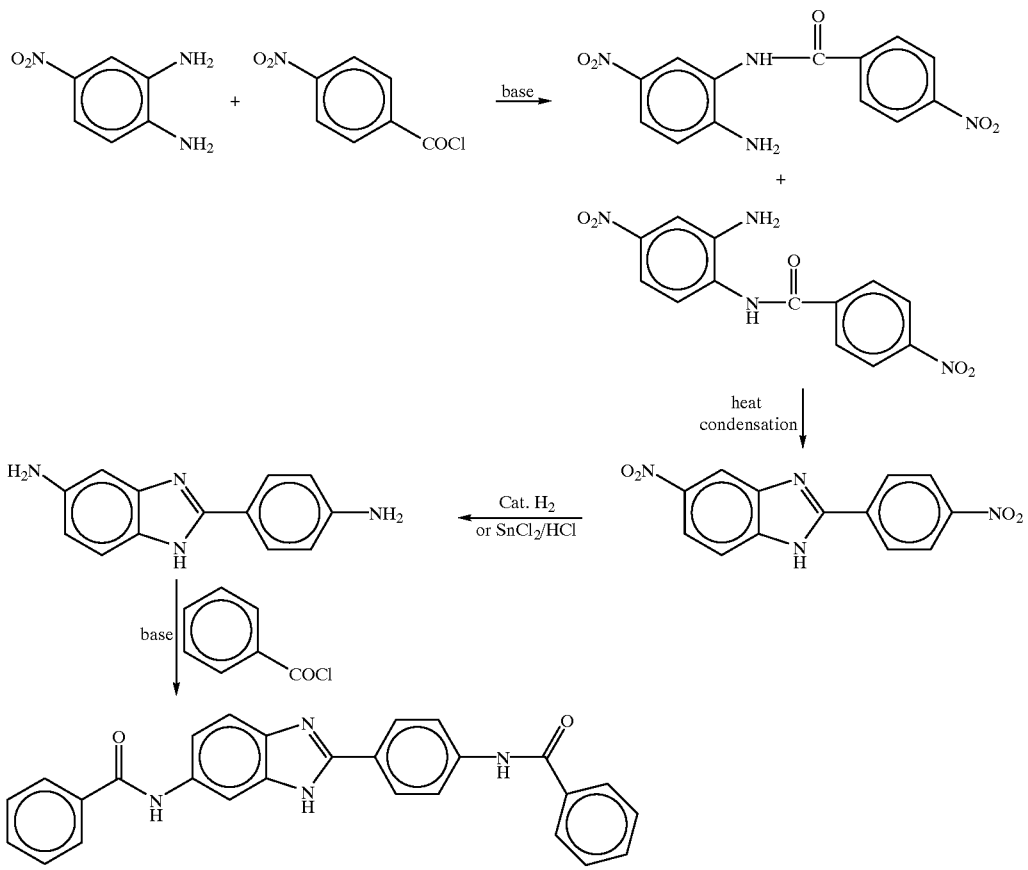

The reactant can be obtained from a commercial supplier, such as Aldrich Chemical Company, catalog number 10,889-9. Modifications can be prepared by conventional reactions, well known in the field.

Another family of compounds active in the suppressing the IgE response are represented by formula X(1):

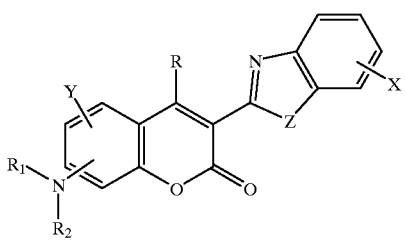

X(1)

wherein X and Y are selected independently from the group consisting of H, alky, alkoxy, aryl, substituted aryl, heteroaryl, substituted heteroaryl, hydroxy, halogen, $NO_2$, $CF_3$, $OCF_3$, $NH_2$, $NHR_3$, $NR_3R_4$ and CN. Z is O, S, NH, and N—R'. R is selected from the group consisting of H, alkyl, halogen, alkoxy, $CF_3$ and $OCF_3$. R' is selected from the group consisting of H, alkyl, aminoalkyl, and dialkylaminoalkyl, and $R_1$ and $R_2$ are independently selected from the group consisting of H, alkyl, aminoalkyl, dialkylaminoalkyl, hydroxyalkyl, alkoxyalkyl, cycloalkyl, oxacycloalkyl and thiocycloalkyl.

Several compounds (X.1–9) encompassed within the broad family defined by formula X(1) were prepared and found to be active in suppressing IgE. They are defined by formula X(2) with X, R1 and R2 specified in Table 2:

TABLE 2

X(2)

| | $R_1$ | $R_2$ | X |
|---|---|---|---|
| IX.1 | H | 5-Cl | NH |
| X.2 | 6-Cl | 5-Cl | NH |
| X.3 | H | 5-$CH_3$ | O |
| X.4 | 5-$SO_2CH_2CH_3$ | H | O |
| X.5 | H | 6-$OCH_3$ | O |
| X.6 | H | 5-COOH | NH |
| X.7 | H | 6-$OCH_3$ | O |
| X.8 | H | 4-$CH_3$ | O |
| X.9 | H | 5-$CF_3$ | N—CH($CH_3$)$_2$ |

Compounds of formula X may be synthesized by any conventional reactions known in the art. An example of a synthesis reaction is shown below:

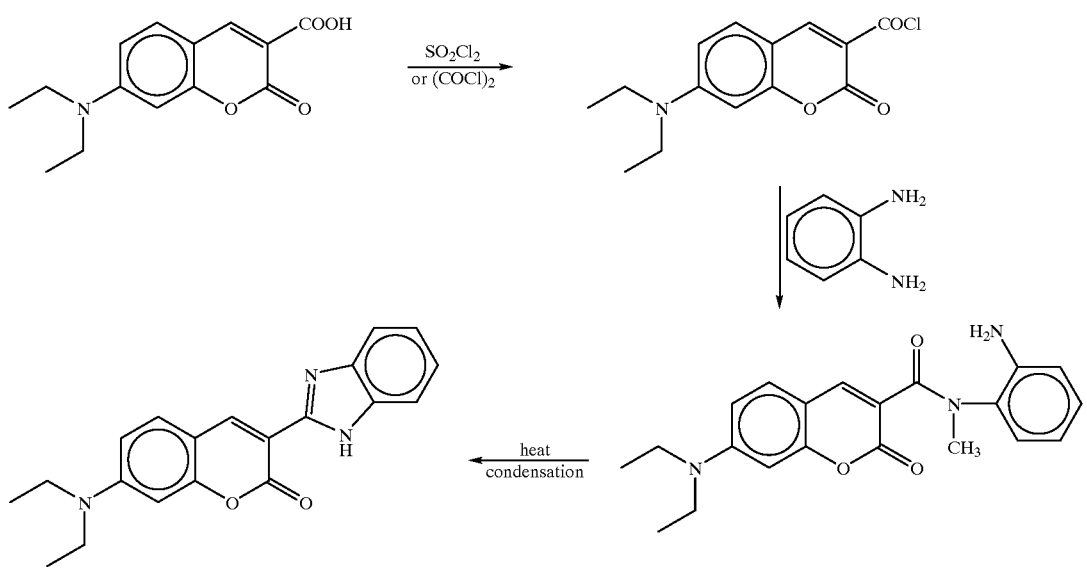

The reactants can be obtained from a commercial suppliers, such as Molecular Probes Inc., catalog number D-1421 and Aldrich Chemical Company, catalog number 39,898-5. Modifications can be prepared by conventional reactions, well known in the field.

Another synthesis that was used successfully to produce 3-(6'-methyl-2'benzoxazolyl)-7-diethylamino-2H-1-benzopyran-2-one ($R_1$=H, $R_2$=6-$CH_3$ and X=O) involved mixing 7-diethylamino-2-oxo-2H-1benzopyran-3-carboxylic acid (2.5 g, 9.57 mol) [CIBA Ltd., British Patent 914719; Chem Abs. 61 (1964) 3242e; Ayyangar et al., Dyes & Pigments, 13:301–316 (1990)], 2-hydroxy-4-methylaniline (1.18 g, 9.57 mol) and PPA (25 ml). The mixture was stirred at 180° C. for 5.0 hr, then poured into ice-water (400 ml), neutralized with 10% NaOH and 10% $NaHCO_3$ to pH 8.5 and extracted with $CHCl_3$ (4×400 ml). The chloroform extract was dried and treated with charcoal, filtered and concentrated. The residue was recrystallized from hexane and $CH_2Cl_2$ (1:1) to give 1.75 g, m.p. 189–191° C.

A mixture of 7-diethylamino-2-oxo-2H-1benzopyran-3-carboxylic acid, the appropriate substituted o-aminophenol or o-phenylenediamine and PPA were stirred at 180° C. for several hrs, as detailed above for each of the species X. 1–9.

Another group of compounds active in the suppressing the IgE response are represented below. In particular, substituted 1,3,5-triazine compounds are illustrated in XI(1):

XI(1)

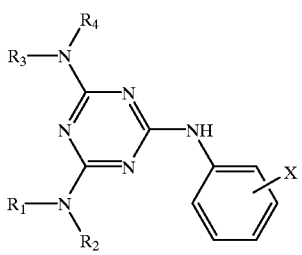

where $R_1$ and $R_2$ are independently H, alkyl, aryl, heteroaryl, arylalkyl or heteroarylalkyl, where X is H, halogen, alkoxy, alkyl, $CF_3$, $NO_2$, CN or $OCF_3$, and where $R_3$ and $R_4$ are independently H, alkyl, cycloalkyl, oxacycloalkyl or thiocycloalkyl.

General modification of the 1,2,3-triazine ring, useful in the present invention is represented by formula XI(2):

XI(2)

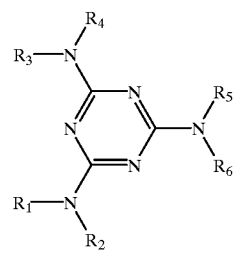

where $R_1$, $R_2$, $R_3$, $R_4$, $R_5$ and $R_6$ are the same or different and selected independently from the group consisting of alkyl, cycloalkyl, oxacycloalkyl, thiocycloalkyl, aryl, heteroaryl, arylalkyl, heteroarylalkyl, substituted aryl and substituted heteroaryl.

One compound encompassed by formula XI was prepared and found to be active in suppressing IgE; it is represented by formula XI.1:

XI.1

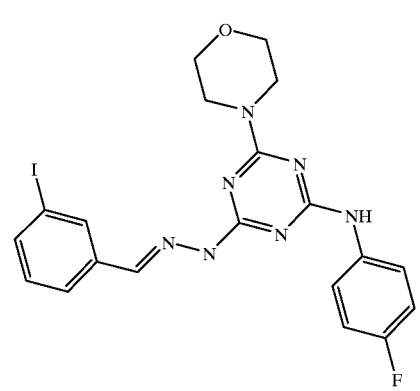

Compounds of formula XI may be synthesized by any conventional reactions known in the art. An example of a synthesis reaction is shown below:

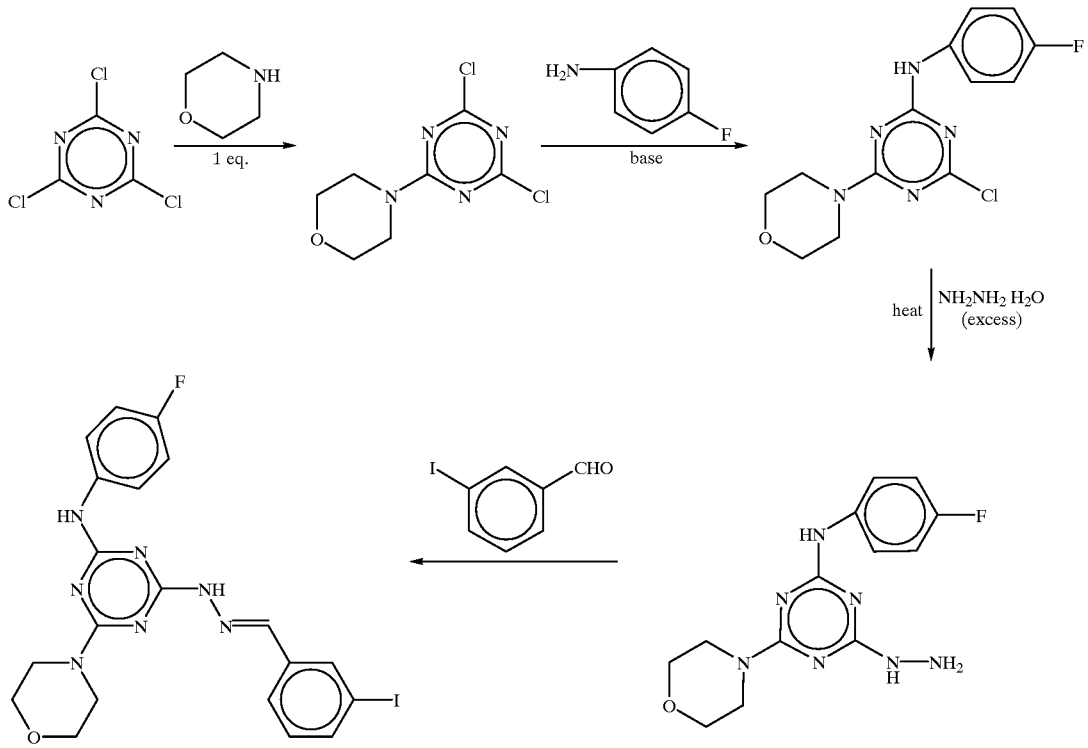

The reactant can be obtained from a commercial suppliers, such as Aldrich Chemical Company, catalog number C9,550-1. Modifications can be prepared by conventional reactions.

Another group of compounds which are active in inhibiting the IgE response in the ex vivo and in vivo assays is represented by formula XII:

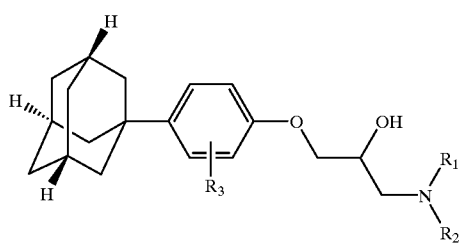

XII where $R_1$ and $R_2$ are independently H, alkyl, aryl, alkylaryl, substituted alkyl, substituted arylalkyl, dialkyl and aminoalkyl, and where $R_3$ is H, alkyl, aryl, halogen, $CF_3$, $OCF_3$, CN, $NO_2$, $NH_2$, NHR, carboxy, carboxyalkyl, alkoxy, heteroaryl, fused aryl, fused heteroaryl and the like.

A series of compounds encompassed within the definition of formula XII were synthesized according to the following reaction, where the compounds are defined by the substitutions provided in Table 3.

To a solution of 4-(1-adamantyl)-phenol (10 g, 0.044 mol) in DMF (40 ml) at −5° C. was added to solid sodium hydride (1.8 g, 0.077 mol) and DMF (20 ml). After the evolution of gas ceased, epichlorhydrin was added dropwise with stirring. The reaction mixture was stirred for 48 hr and then poured onto cold water (500 ml), extracted with EtOH (3×100 ml), dried, concentrated to give 8.1 g of the desired epoxide. Purity was measured by GC at 94.1%.

The epoxide (1.0 g) was reacted with excess tert-butylamine at 60° C. for 24 hr and worked up as described above to give 1.1 g of the desired product, m.p. 94–96° C.

TABLE 3

|  | $R_1$ | $R_2$ |
|---|---|---|
| XII.1 | H | isopropyl |
| XII.2 | H | 2-(2′,5′-dimethoxy)-phenylethyl |
| XII.3 |  | $R_1 = R_2 =$ thiomorpholine |

Compounds encompassed by formula XII were prepared and found to be active in suppressing IgE; they is represented by formulas XII.1–4:

XII.1

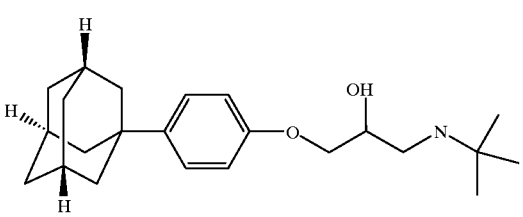

XII.2

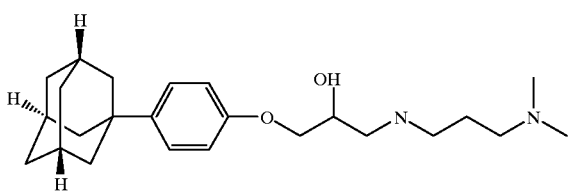

-continued

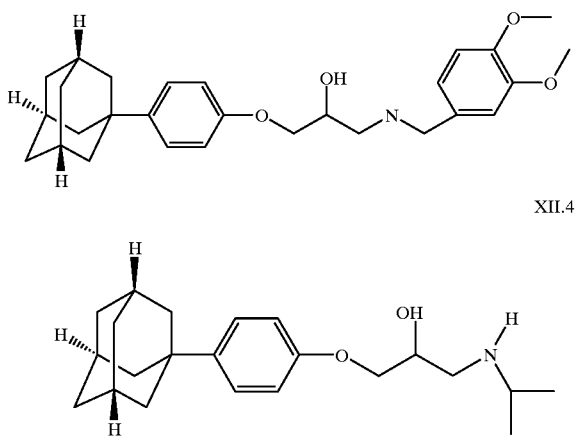

Compounds of formula XII may be synthesized by any conventional reactions known in the art. The above compounds were synthesized according to the reaction illustrated below:

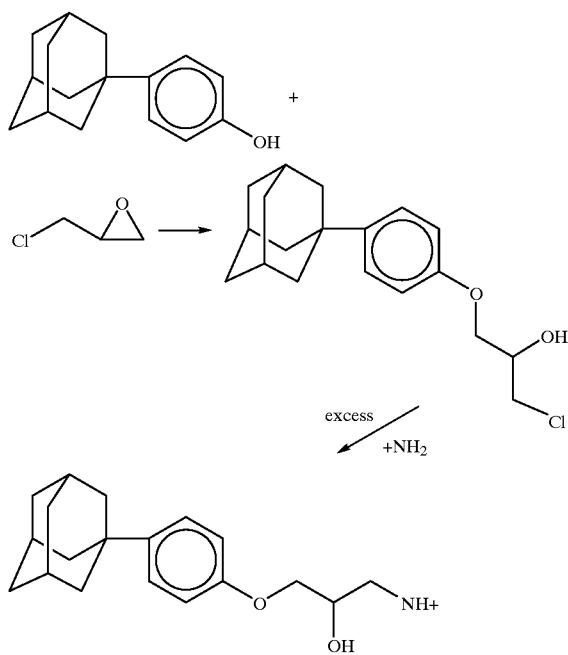

The reactants can be obtained from a commercial suppliers, such as Aldrich Chemical Company, catalog number 39,347-9. Modifications can be prepared by conventional reactions.

Suppression of IgE Response

The inhibitory activity of the small molecules of the present invention were assayed using both the ex vivo and in vivo assays as described above. All of the compounds presented above were active in suppressing the IgE response. In the ex vivo assay, compounds in genuses I-XI produced 50% inhibition at concentrations ranging from 1 pM to 10 $\mu$M. In the in vivo assay, the compounds were effective at concentrations ranging from less than about 0.01 mg/kg/day to about 25 mg/kg/day, when administered in divided doses (e.g., two to four times daily) for at least two to seven consecutive days. Thus, the small molecule inhibitors of the present invention are disclosed as being useful in lowering the antigen-induced increase in IgE concentration, and consequently, in the treatment of IgE-dependent processes such as allergies in general and allergic asthma in particular.

Treatment Regimens

The amount of the IgE inhibitor compound which may be effective in treating a particular allergy or condition will depend on the nature of the disorder, and can be determined by standard clinical techniques. The precise dose to be employed in a given situation will also depend on the choice of compound and the seriousness of the condition, and should be decided according to the judgment of the practitioner and each patient's circumstances. Appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395–407 (1997) and Ohmori et al., *Int. J Immunopharmacol.* 15:573–579 (1993); employing similar ex vivo and in vivo assays for determining dose-response relationships for IgE suppression by naphthalene derivatives; incorporated herein by reference).

Initially, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment, the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In one embodiment of the present invention, an IgE-suppressing compound may be administered in conjunction with one or more of the other small molecule inhibitors disclosed, in order to produce optimal down-regulation of the patient's IgE response. Further, it is envisioned that one or more of the compounds of the present invention may be administered in combination with other drugs already known or later discovered for treatment of the underlying cause as well as the acute symptoms of allergy or asthma. Such combination therapies envisioned within the scope of the present invention include mixing of one or more of the small molecule IgE-inhibitors together with one or more additional ingredients, known to be effective in reducing at least one symptom of the disease condition. In a variation, the small molecule IgE-inhibitors herein disclosed may be administered separately from the additional drugs, but during the same course of the disease condition, wherein both the IgE-inhibitor(s) and the palliative compounds are administered in accordance with their independent effective treatment regimens.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A compound for use in treating or preventing an allergic reaction which is caused by an increase in plasma IgE levels, the compound having a formula:

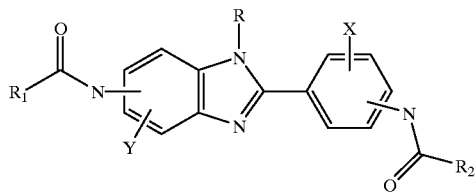

wherein X and Y are independently selected from the group consisting of H, halogen, alkyl, alkoxy, aryl, substituted aryl, hydroxy, amino, alkylamino, cycloalkyl, morpholine, thiomorpholine, nitro, cyano, $CF_3$ and $OCF_3$;

wherein R is selected from the group consisting of H, $CH_3$, $C_2H_5$, $C_3H_7$ and $C_4H_9$; and where $R_1$ and $R_2$ are independently selected from the group consisting of H, alkyl, cycloalkyl, substituted cycloalkyl, polycycloalkyl, substituted polycycloalkyl, aryl, substituted aryl, heteroaryl and substituted heteroaryl, and wherein $R_1$ and $R_2$ are not phenyl groups.

2. The compound of claim 1, having the formula:

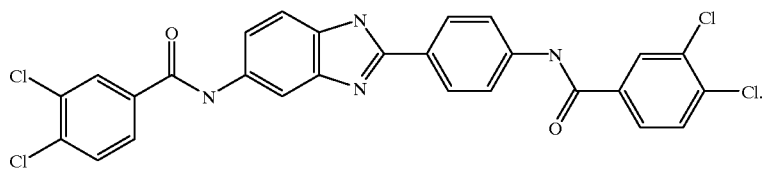

3. The compound of claim 1, having the formula:

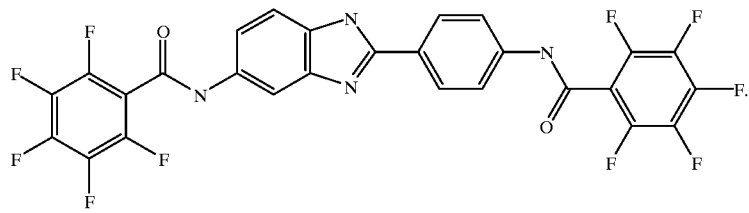

4. A method for treating or preventing an allergic reaction which is caused by an increase in plasma IgE levels in a mammal which comprises administering to said mammal an IgE-suppressing amount of a pharmaceutical formulation comprising a compound having a formula:

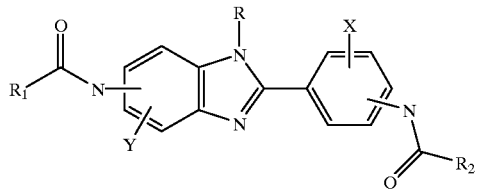

wherein X and Y are independently selected from the group consisting of H, halogen, alkyl, alkoxy, aryl, substituted aryl, hydroxy, amino, alkylamino, cycloalkyl, morpholine, thiomorpholine, nitro, cyano, $CF_3$ and $OCF_3$;

wherein R is selected from the group consisting of H, $CH_3$, $C_2H_5$, $C_3H_7$ and $C_4H_9$; and where $R_1$ and $R_2$ are independently selected from the group consisting of H, alkyl, cycloalkyl, substituted cycloalkyl, polycycloalkyl, substituted polycycloalkyl, aryl, substituted aryl, heteroaryl and substituted heteroaryl.

5. The method of claim 4, wherein said method further comprises administering an additional ingredient which is active in reducing a symptom associated with said allergic reaction.

6. The method of claim 5, wherein said additional ingredient is combined with said pharmaceutical formulation in a pharmaceutically acceptable diluent and co-administered to the mammal.

7. The method of claim 5, wherein said additional ingredient is selected from the group consisting of a $\beta_2$-adrenergic agonist, an antihistamine, a phosphodiesterase inhibitor, an anticholinergic agent, a corticosteroid, an inflammatory mediator release inhibitor and a leukotriene receptor antagonist.

8. The method of claim 4, wherein the compound is administered at a dose of about 0.01 mg to about 100 mg per kg body weight per day.

9. The method of claim 8, wherein said dose is administered in divided doses at regular periodic intervals for at least two consecutive days.

10. The method of claim 4, wherein the pharmaceutical formulation comprises a compound having the formula:

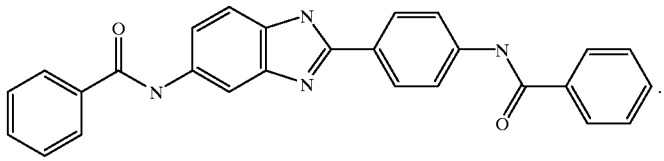

11. The method of claim 4, wherein the pharmaceutical formulation comprises a compound having the formula:

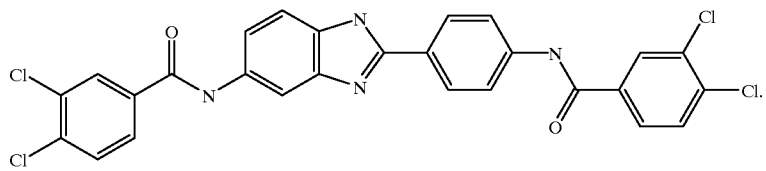

12. The method of claim 4, wherein the pharmaceutical formulation comprises a compound having the formula:

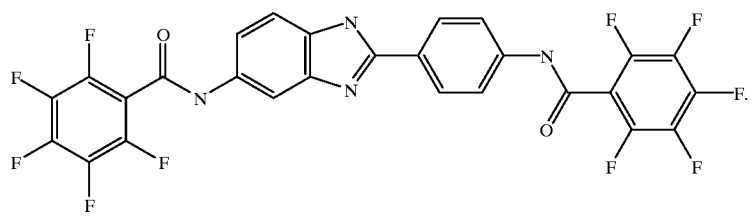

13. A method for treating or preventing asthma which is caused by an increase in plasma IgE levels in a mammal which comprises administering to said mammal an IgE-suppressing amount of a pharmaceutical formulation comprising a compound having a formula:

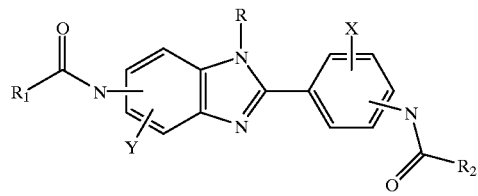

wherein X and Y are independently selected from the group consisting of H, halogen, alkyl, alkoxy, aryl, substituted aryl, hydroxy, amino, alkylamino, cycloalkyl, morpholine, thiomorpholine, nitro, cyano, $CF_3$ and $OCF_3$; wherein R is selected from the group consisting of H, $CH_3$, $C_2H_5$, $C_3H_7$ and $C_4H_9$; and where $R_1$ and $R_2$ are independently selected from the group consisting of H, alkyl, cycloalkyl, substituted cycloalkyl, polycycloalkyl, substituted polycycloalkyl, aryl, substituted aryl, heteroaryl and substituted heteroaryl.

14. The method of claim 13, wherein said method further comprises administering an additional ingredient which is ictive in reducing a symptom associated with asthma.

15. The method of claim 14, wherein said additional ingredient is selected from the group consisting of a $\beta_2$-adrenergic agonist, an antihistamine, a phosphodiesterase inhibitor, an anticholinergic agent, a corticosteroid, an inflammatory mediator release inhibitor and a leukotriene receptor antagonist.

* * * * *